US008874192B2

(12) United States Patent
Hundley et al.

(10) Patent No.: US 8,874,192 B2
(45) Date of Patent: *Oct. 28, 2014

(54) NON-INVASIVE IMAGING FOR DETERMINATION OF GLOBAL TISSUE CHARACTERISTICS

(71) Applicant: Wake Forest University Health Sciences, Winston-Salem, NC (US)

(72) Inventors: William Gregory Hundley, Winston-Salem, NC (US); Craig A. Hamilton, Lewisville, NC (US); Kimberly Lane, Advance, NC (US); Tim Morgan, Clemmons, NC (US); Frank Torti, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,581

(22) Filed: Aug. 7, 2013

(65) Prior Publication Data

US 2013/0324831 A1    Dec. 5, 2013

Related U.S. Application Data

(63) Continuation of application No. 12/019,457, filed on Jan. 24, 2008, now Pat. No. 8,532,739, which is a continuation of application No. 11/051,304, filed on Feb. 4, 2005, now Pat. No. 7,333,845.

(60) Provisional application No. 60/542,547, filed on Feb. 6, 2004.

(51) Int. Cl.
*A61B 5/05* (2006.01)
*G01R 33/56* (2006.01)
(Continued)

(52) U.S. Cl.
CPC .............. *A61B 5/0033* (2013.01); *G01R 33/56* (2013.01); *A61B 5/4519* (2013.01);
(Continued)

(58) Field of Classification Search
None
See application file for complete search history.

(56) References Cited

U.S. PATENT DOCUMENTS 5,233,299 A    8/1993  Souza et al.
5,333,244 A    7/1994  Harashima
(Continued)

FOREIGN PATENT DOCUMENTS

JP    2003325458    11/2003
WO   WO 01/87173    11/2001
(Continued)

OTHER PUBLICATIONS

"General Principals of Software Validation; Final Guidance for Industry and FDA Staff" U.S. Dept of Health and Human Services, Food and Drug Administration, Center for Devices and Radiological Health, Center for Biologics and Evaluation Research, 47 pages (Jan. 11, 2002).

(Continued)

*Primary Examiner* — Parikha Mehta
(74) *Attorney, Agent, or Firm* — Myers Bigel Sibley & Sajovec, P.A.

(57) ABSTRACT

Evaluating tissue characteristics including identification of injured tissue or alteration of the ratios of native tissue components such as shifting the amounts of normal myocytes and fibrotic tissue in the heart, identifying increases in the amount of extracellular components or fluid (like edema or extracellular matrix proteins), or detecting infiltration of tumor cells or mediators of inflammation into the tissue of interest in a patient, such as a human being, is provided by obtaining a first image of tissue including a region of interest from a first acquisition, and obtaining a second image of the tissue including the region of interest during a second, subsequent acquisition. The subsequent acquisition may be obtained after a period of time to determine if injury has occurred during that period of time. Such a comparison may include comparison of mean, average characteristics, histogram shape, such as skew and kurtosis, or distribution of intensities within the histogram.

26 Claims, 9 Drawing Sheets

(51) Int. Cl.
G06T 7/00 (2006.01)
A61B 6/00 (2006.01)
G06T 7/40 (2006.01)
A61B 5/055 (2006.01)
A61B 5/00 (2006.01)
A61B 6/03 (2006.01)
G01R 33/28 (2006.01)

(52) U.S. Cl.
CPC .......... *G06T 7/0014* (2013.01); *G06T 2200/24* (2013.01); *A61B 6/503* (2013.01); *A61B 6/032* (2013.01); *G06T 2207/10088* (2013.01); *A61B 5/42* (2013.01); *G06T 7/401* (2013.01); *A61B 5/055* (2013.01); *A61B 6/504* (2013.01); *G01R 33/281* (2013.01); *G06T 2207/30048* (2013.01)
USPC .......... 600/411; 600/407; 600/420; 600/431; 382/170

(56) References Cited

U.S. PATENT DOCUMENTS

| | | | |
|---|---|---|---|
| 5,732,121 | A | 3/1998 | Takeo et al. |
| 5,871,013 | A | 2/1999 | Wainer et al. |
| 6,368,285 | B1 | 4/2002 | Osadchy et al. |
| 6,415,046 | B1 | 7/2002 | Kerut, Sr. |
| 7,106,892 | B2 | 9/2006 | Breeuwer et al. |
| 7,187,789 | B2 | 3/2007 | Takeo |
| 7,258,670 | B2 | 8/2007 | Bardy |
| 7,301,016 | B2 | 11/2007 | Meyers et al. |
| 7,330,601 | B2 | 2/2008 | Shin et al. |
| 7,333,845 | B2 | 2/2008 | Hundley et al. |
| 7,396,654 | B2 | 7/2008 | Hayes et al. |
| 7,463,919 | B2 | 12/2008 | Hamilton et al. |
| 7,747,308 | B2 | 6/2010 | Hundley et al. |
| 2003/0009098 | A1 | 1/2003 | Jack et al. |
| 2003/0063787 | A1 | 4/2003 | Natanzon et al. |
| 2005/0075567 | A1 | 4/2005 | Skyba et al. |
| 2005/0215883 | A1 | 9/2005 | Hundley et al. |

FOREIGN PATENT DOCUMENTS

| | | |
|---|---|---|
| WO | WO 03/061466 | 7/2003 |
| WO | WO 2004/026140 | 4/2004 |
| WO | WO 2005/077263 | 8/2005 |

OTHER PUBLICATIONS

Able Software Corp. 3D-Doctor User Manual, Part II, Oct. 16, 2003, Retrieved from the Internet: URL: http://web.archive.org/web/20031016035402/www.ales.com/3d-doctor/manual2.pdf, retrieved on Aug. 30, 2007.
Bellenger et al. "Reduction in Sample Size for Studies of Remodeling in Heart Failure by the Use of Cardiovascular Magnetic Resonance" *J Cardiovascular Mangn Reson*2(4): 271-278 (2000) (Abstract).
Bristow et al. "Doxorubicin Cardiomyopathy: Evaluation by Phonocardiography, Endomyocardial Biopsy, and Cardiac Catheterization" *Annals of Internal Medicine*88: 168-175 (1978).
Cardinale et al. "Myocardial Injury Revealed by Plasma Troponin I in Breast Cancer Treated with High-Dose Chemotherapy" *Annals of Oncology*13: 710-715 (2002).
Cerqueira et al. "Standardized Myocardial Segmentation and Nomenclature for Tomographic Imaging of the Heart: A Statement for Healthcare Professionals from the Cardiac Imaging Committee of the Council on Clincial Cardiology of the American Heart Association" *Circulation*150: 539-542 (2002).
Choi et al. "Transmural Extent of Acute Myocardial Infarction Predicts Long-Term Improvement in Contractile Function" *Circulation*104: 1101-1107 (2001).
Chuang et al. "Importance of Imaging Method Over Imaging Modality in Noninvasive Determination of Left Ventricular Volumes and Ejection Fraction: Assessment by Two- and Three-Dimensional Echocardiography and Magnetic Resonance Imaging" *Journal of the American College of Cardiology*35(2): 477-484 (2000).
Darty et al. "Nursing Responsibilities During Cardiac Magnetic Resonance Imaging" Department of Internal Medicine (Cardiology Section) and Radiology at the Wake Forest University School of Medicine (no date).
Del Carlo et al. "Cardiac Troponins in Congestive Heart Failure" *American Heart Journal*138: 646-653 (1999).
Dombernowsky et al. "Doxorubicin and Paclitaxel, a Highly Active Combination in the Treatment of Metastatic Breast Cancer" *Seminars in Oncology*23(5 suppl 11): 23-27 (1996).
Gehl et al. "Paclitaxel and Doxorubicin in Metastatic Breast Cancer" *Seminars in Oncology*23(6 suppl 15): 35-38 (1996).
Gerber et al. "Relation Between Gd-DTPA Contrast Enhancement and Regional Inotropic Response in the Periphery and Center of Myocardial Infarction" *Circulation*104:998-1004 (2001).
Gianni et al. "Cardiac Function Following Combination Therapy with Taxol (T) and Doxorubicin (A) for Advanced Breast Cancer (ABC)" *Proceedings of ASCO*vol. 17 (1998) (Abstract).
Gianni et al. "Paclitaxel by 3-Hour Infusion in Combination with Bolus Doxorubicin in Women with Untreated Metastatic Breast Cancer: High Antitumor Efficacy and Cardiac Effects in a Dose-Finiding and Sequence-Finding Study" *Journal of Clinical Oncology*13(11): 2688-2699 (1995).
Gottdiener et al. "Doxorubicin Cardiotoxicity: Assessment of Late Left Ventricular Dysfunction by Radionuclide Cineangiography" *Annals of Internal Medicine*94(part 1): 430-435 (1981).
Hamilton et al. "Is Imaging at Intermediate Doses Necessary During Dobutamine Stress Magnetic Resonance Imaging?" *Journal of Cardiovascular Magnetic Resonance*3(4): 297-302 (2001).
Herlidou-Meme, S. et al., MRI texture analysis on texture test objects, normal brain and intracranial tumors, Magnetic Resonance Imaging, (2003), pp. 989-993, vol. 21.
Hochster et al. "Cardiotoxicity and Cardioprotection During Chemotherapy" *Current Science*7: 304-309 (1995).
Hortobagyi "Treatment of Breast Cancer" *The New England Journal of Medicine*339(14): 974-984(1998).
Hundley et al. "Magnetic Resoance Imaging Determination of cardiac Prognosis" *Circulation*106: 2328-2333 (2002).
Hundley et al. "Magnetic Resonance Imaging Assessment of the Severity of Mitral Regurgitation: Comparison with Invasive Techniques" *Circulation*92: 1151-1158 (1995).
Hundley et al. "Relation of Cardiac Prognosis to Segment Location with Apical Left Ventricular Ischemia" *The American Journal of Cardiology*92: 1206-1208 (2003).
Hundley et al. "Utility of Fast Cine Magnetic Resoance Imaging an display for the Detection of Myocardial lschemia in patients Not Well Suited for Second Harmonic Stress Echocardiography" *Circulation*100: 1697-1702 (1999).
Jacobson et al. "Magnetic Resonance Imaging of the Cardiovascular System: Present State of the Art and Future Potential" *JAMA*259(2): 253-259 (1988).
Jensen et al. "Functional Monitoring of Anthracycline Cardiotoxicity: A Prospective, Blinded, Long-Term Ovservational Study of Outcome in 120 patients" *Annals of Oncology*13: 699-709 (2002).
Jirak, Daniel, et al., Texture Analysis of Human Liver, Journal of Magnetic Resonance Imaging, vol. 15, pp. 68-74 (2002).
Judd et al. "Physiological basis of Myocardial Contrast Enhancement in Fast Magnetic Resonance Images of 2-Day-Old Reperfused Canine Infarcts" *Circulation*92: 1902-1910 (1995).
Kellman et al. "Phase-Sensitive Inversion Recover for Detecting Myocardial Infarction Using Gadolinium-Delayed Hyperenhancement" *Magnetic Resonance in Medicine*47: 372-383 (2002).
Kim et al. "The Use of Contract-Enhanced Magnetic Resonance Imaging to Identify Reversible Myocardial Dysfunction" *New England Journal of Medicine*343: 1445-1453 (2000).
Leandro et al. "Cardiac Dysfunction Late After Cardiotoxic Therapy for Childhood Cancer" *The American Journal of Cardiology*74:1152-1156 (1994).
Lebwhol et al. "New Developments in Chemotherapy of Advanced Breast Cancer" *Annals of Oncology*10(suppl 6): S139-S146 (1999).

(56) References Cited

OTHER PUBLICATIONS

Lipshultz et al. "Late Cardiac Effects of Doxorubicin Therapy for Acute Lymphoblastic Leukemia in Childhood" *The New England Journal of Medicine* 324(12): 808-815 (1991).
Longmore et al. "Dimensional Accuracy of Magnetic Resonance in Studies of the Heart" *The Lancet* pp. 1360-1362 (Jun. 15, 1985).
Lorenz et al. "Normal Human Right and Left Ventricular Mass, Systolic Function, and Gender Differences by Cine Magnetic Resonance Imaging" *J Cardiovascular Magn Reson* 1(1): 7-21 (1999).
Maisel et al. "B-Type Natriuretic Peptide Levels: Diagnostic and Prognostic in Congestive Heart Failure: What's Next?" *Circulation* 150: 2328-2331 (2002).
Martin et al. "Imaging Cardiac Structure and Pump Function" *Cardiac Magnetic Resonance Imaging* 16(2): 135-160 (1998).
McDonagh et al. "Biochemical Detection of Left-Ventricular Systolic Dysfunction" *The Lancet* 351: 9-13 (1998).
Missov et al. "Cardiac Troponin I in Patients with Hematologic Malignancies" *Coronary Artery Disease* 8: 537-541 (1997).
Osoba et al. "Effects on Quality of Life of Combined Trastuzumab and Chemotherapy in women with Metastatic Breast Cancer" *Journal of Clinical Oncology* 20(14): 3106-3113 (2002).
Pagani et al. "Dose-Finding Study of Epidoxorubicin and Docetaxel as First-Line Chemotherapy in Patients with Advanced Breast Cancer" *Annals of Oncology* 10: 539-545 (1999).
Pattynama et al. "Left Ventricular Measurements with Cine and Spin-Echo MR Imaging: A Study of Reproducibility with Variance Component Analysis" *Radiology* 187: 261-268 (1993).
Rector et al. "Assessment of Patient Outcome with the Minnesota Living Heart Failure Questionnaire: Reliability and Validity During Randomized, Double-Blind, Placebo-Controlled Trial of Pimobendan" *American Heart Journal* 124: 1017-1025 (1992).
Rehr et al. "Left Ventricular Volumes Measured by MR Imaging" *Radiology* 156: 717-719 (1985).
Rerkpattanapipat et al. "Clinical Utility of Assessments of Left Ventricular Systolic Function and Coronary Arterial Blood Flow During Pharmacological Stress with Magnetic Resonance Imaging" *Topics in Magnetic Resonance Imaging* 11(6): 399-405 (2000).
Rischin et al. "A Phase I and Pharmacokinetic Study of Paclitaxel and Epirubicin in Advanced Cancer" *Investigational New Drugs* 17: 73-80 (1999).
Sakuma, et al., Functional MRI diagnosis for heart, New Medical Care, Jun. 11, 2001, vol. 28, No. 6, pp. 50-53.
Schwartz et al. "Congestive Heart Failure and Left Ventricular Dysfuntion Complicating Doxorubicin Therapy" *The American Journal of Medicine* 82: 1109-1118 (1987).
Sechetem et al. "Measurement of Right and Left Ventricular Volumes in healthy Individuals with cine MR Imaging" *Radiology* 163: 697-702 (1987).
Semelka et al. "Interstudy Reproducibility of Dimensional and Functional Measurements Between Cine Magnetic Resonance Studies in the Morphologically Abnormal Left Ventricle" *American Heart Journal* 119: 1367-1373 (1990).
Shek et al. "Paclitaxel-Induced Cardiotoxicity" *Arch Pathol Lab Med* 120: 89-91 (1996).
Singal et al. "Doxorubicin-Induced Cardiomyopathy" *The New England Journal of Medicine* 339(13): 900-905 (1998).
Slamon et al. "Use of Chemotheraphy Plus a Monocolonal Antibody Against Her2 for Matastatic Breast Cancer that Overrexpresses Her2" *The New England Journal of Medicine* 344(11): 783-792 (2001).
Stratemeier et al. "Ejection Fraction Determination by MR Imaging: Comparison with Left Ventricular Angiography" *Radiology* 158: 775-777 (1986).
Suter et al. "Detection of Anthracycline-Induced Cardiotoxicity: Is There Light at the End of the Tunnel?" *Annals of Oncology* 13: 647-649 (2002).
Torti et al. "Cardotoxicity of Epirubicin and Doxorubicin: Assessment by Endomyocardial Biopsy" *Cancer Research* 46: 3722-3727 (1986).
Torti et al. "Weekly Doxorubicin in Endocrine-Refractory Carcinoma of the Prostate" *Journal of Clinical Oncology* 1(8): 477-482 (1983).
Unverferth et al. "Early Changes in Human Myocardial Nuclei after Doxorubicin" *Cancer* 52:215-221 (1983).
Valdivieso et al. "Increased Therapeutic Index of Weekly Doxorubicin in the Therapy of Non-Small Cell Lung Cancer: A Prospective, Randomized Study" *Journal of Clinical Oncology* 2(3): 207-214 (1984).
Von Hoff et al. "Daunomycin-Induced Cardiotoxicity in Children and Adults" *The American Journal of Medicine* 62:200-208 (1977).
Von Hoff et al. "Risk Factors for Doxorubicin-Induced Congestive Heart Failure" *Annals of Internal Medicine* 91: 710-77 (1979).
Wu et al. "Visualisation of Presence, Location, and Transmural Extent of Healed Q-Wave and Non-Q-Wave Myocardial Infarction" *The Lancet* 357: 21-28 (2001).
Wassmuth et al., *Subclinical cardiotoxic effects of anthracyclines as assessed by magnetic resonance imaging—A pilot study*, American Heart Journal, Jun. 2001, vol. 141, No. 6, pp. 1007-1013, (Jun. 2001).
Saeed M et al., *Reversible and irreversible injury in the reperfused myocardium: differentiation with contrast material-enhanced MR imaging*, Radiology, Oak Brook, IL, US, vol. 175, No. 3, pp. 633-637, (Apr. 1990).
Gerber Bernhard L et al., *Accuracy of contrast-enhanced magnetic resonance imaging in predicting improvement of regional myocardial function in patients after acute myocardial infarction*, Circulation, vol. 106, No. 9, pp. 1083-1089, (Aug. 27, 2002).

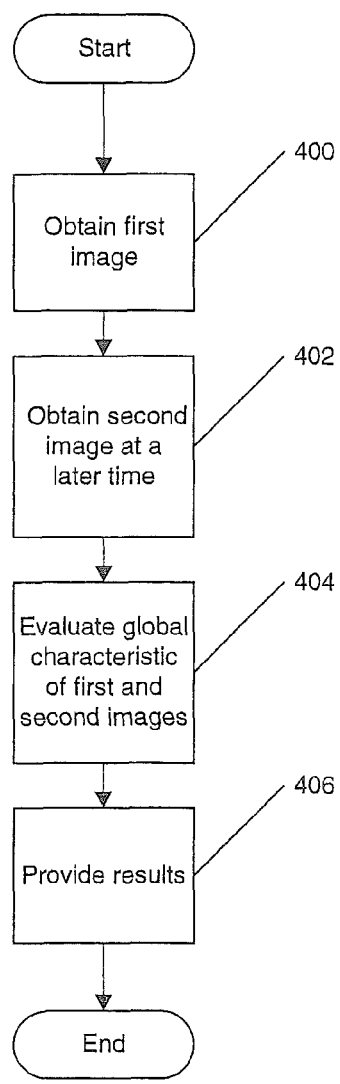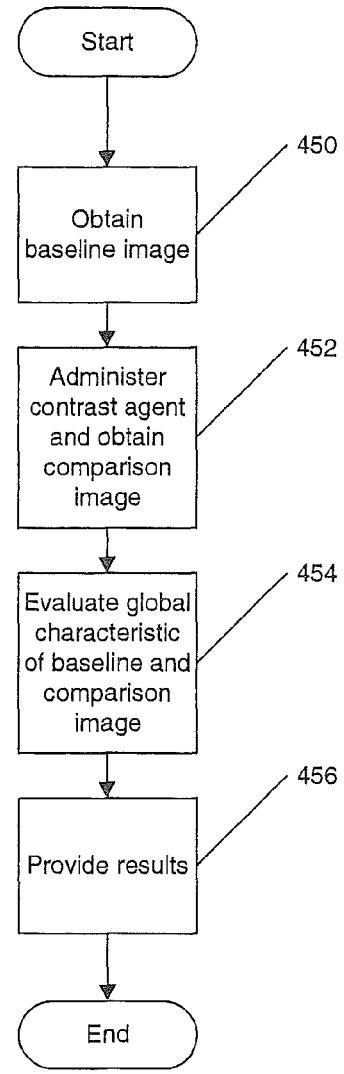
Figure 4A
Figure 4B

NON-INVASIVE IMAGING FOR DETERMINATION OF GLOBAL TISSUE CHARACTERISTICS

RELATED APPLICATIONS AND CLAIM OF PRIORITY

This application is a continuation of U.S. patent application Ser. No. 12/019,457 filed Jan. 24, 2008, which issued as U.S. Pat. No. 8,532,739 on Sep. 10, 2013, which is a continuation of U.S. patent application Ser. No. 11/051,304 filed Feb. 4, 2005, which issued as U.S. Pat. No. 7,333,845 on Feb. 19, 2008, which claims the benefit of priority of U.S. Provisional Patent Application Ser. No. 60/542,547 filed Feb. 6, 2004, the disclosures of which are incorporated herein by reference as if set forth in its entirety.

FIELD OF THE INVENTION

The present invention is related to diagnostics and more particularly to the detection of global tissue characteristics, such as global tissue injury.

BACKGROUND OF THE INVENTION

Doxorubicin is an anthracycline antibiotic isolated from a soil microorganism. Its anti-tumor effects are related to interactions with the enzyme topoisomerase-2 and production of double strand DNA breaks. In addition, this agent generates intracellular free radicals that are highly cytotoxic. Doxorubicin is considered one of the most broadly active antitumor agents. Not only is Doxorubicin typically considered an important element in modern therapy of breast, soft tissue sarcomas and other solid tumors, it is thought to be an important element of curative combination chemotherapy for acute leukemia, Hodgkin's disease, non-Hodgkin's lymphoma, and many childhood cancers. Thus, for many individuals with advanced stages of cancer, Doxorubicin serves as an important part of their medical regimen.

Administration of Doxorubicin therapy is generally limited in adults and children by a cumulative dose dependent cardiotoxicity. Irreversible cardiomyopathy with serious congestive heart failure can be a significant risk in patients who receive doses in excess of 500-550 mg/m$^2$. Unfortunately, the dose that precipitates congestive heart failure varies widely (ranging from 30-880 mg/m$^2$ in a report of 1487 patients studied over a seven year period). Those subjects with advanced age or mild reductions in left ventricular systolic function at rest (left ventricular ejection fraction [LVEF] ≤50%), are at greatest risk. In western industrialized countries, it is typically older subjects with cancer and some degree of underlying heart disease whom often are in greatest need for Doxorubicin therapy, but for whom medication may be withheld due to potential cardiotoxicity.

One method for detection of Doxorubicin-induced cardiomyopathy is intramyocardial biopsy with concomitant left and right ventricular pressure measurements made during cardiac catheterization. Unfortunately, this method involves an invasive procedure and may not be well suited for repetitive measurements over time. Radionuclide ventriculography is also widely used to screen those individuals at risk for developing Doxorubicin-induced cardiomyopathy. Individuals who develop a reduction in LVEF of 10% or greater or those individuals who have a fall in ejection fraction to lower than 50% during treatment are at greatest risk for developing irreversible cardiotoxicity. While this information is useful as a potential screening technique, for some individuals, the drop observed in LVEF occurs too late to avert the development of irreversible cardiomyopathy. For this reason, the total dose of Doxorubicin may be unduly limited for patients receiving chemotherapy. Importantly for many individuals, Doxorubicin therapy is often stopped before patients derive maximal benefit of the drug regimen. A noninvasive, widely available method for accurately detecting those individuals whom go on to develop cardiotoxicity would have marked clinical utility.

During the past 7 years, investigators have established the utility of MRI for identifying necrotic tissue within the left ventricle in patients sustaining myocellular injury. This technique incorporates the acquisition of gradient-echo pulse sequences with nonselective preparatory radiofrequency pulses after intravenous administration of Gadolinium chelates. In regions of myocardial necrosis, heightened signal intensity occurs on images collected 20 minutes after contrast administration that corresponds to expansion of extracellular volume due to myocellular membrane disruption and increased capillary permeability. This methodology has been utilized to identify transmural myocellular necrosis in patients sustaining acute or chronic Q-wave (ST-segment elevation), and subendocardial (non-transmural) injury in patients sustaining a non-Q-wave (non ST-segment elevation) myocardial infarction. The amount of necrosis found during MRI displays an inverse relationship with recovery of systolic thickening after coronary arterial revascularization. The absence of Gadolinium hyperenhancement 20 minutes after contrast administration is associated with myocardial viability and subsequent improvement in left ventricular contraction after sustaining a ST-segment or non ST-segment elevation myocardial infarction. Although some felt delayed enhancement techniques may overestimate regions of myocellular necrosis in the acute infarct, recently, a tagging study in animals indicated that delayed enhancement techniques do identify early myocellular necrosis after myocardial infarction (MI). It is believed that, in border zones of infarcts, dead cells may move due to tethering from adjacent live regions.

With MRI, cardiac structure can be imaged and LV function directly assessed with high temporal and spatial resolution. Since acoustic windows do not limit image acquisition, the utility of MRI is high particularly in subjects with a large or unusual body habitus. This heightened clarity of the images allows investigators to perform quantitative measures of LV structure and function with higher precision than that achieved with radionuclide and ultrasound techniques. A 5% change in LVEF in patients with reduced LV function can be detected with 90% power at ap-value of 0.05 with a sample size of 5 patients per group in a parallel study design. Depending upon operator experience, the same 5% change in LVEF requires an echocardiographic assessment of >100 subjects per group in the same study design. Similarly, the heightened spatial resolution (1 mm$^2$ pixel sizes) achieved with delayed enhancement MRI techniques allows for the detection of micro-infarcts that heretofore may have only been appreciated as cardiac enzymatic elevations detected in serum samples, but not visualized with radionuclide or echocardiographic techniques.

In delayed enhancement imaging a contrast agent is administered to a patient and an image is acquired after the contrast agent has had an opportunity to be distributed to area that is to be imaged such that the contrast agent remains in injured tissue but does not remain in healthy tissue. Such delayed enhancement imaging may be used, for example, to identify myocardial infarcts as the necrotic tissue of the infarct region will retain the contrast agent while the contrast agent will be purged from the healthy tissue. As such, the infarct may appear as a localized region of higher intensity. Conventionally, delayed enhancement imaging may be used to identify localized regions of tissue damage in tissues such as cardiac tissue, brain tissue, nerve tissue or the like.

SUMMARY OF THE INVENTION

Embodiments of the present invention provide methods, systems and/or computer program products for evaluating tissue characteristics including identification of injured tissue or alteration of the ratios of native tissue components such as shifting the amounts of normal myocytes and fibrotic tissue in the heart, identifying increases in the amount of extracellular components or fluid (like edema or extracellular matrix proteins), or detecting infiltration of tumor cells or mediators of inflammation into the tissue of interest in a patient, such as a human being, by obtaining a first image of tissue including a region of interest from a first acquisition, for example, after administration of a contrast agent to the patient, and obtaining a second image of the tissue including the region of interest during a second, subsequent acquisition, for example, after administration of a contrast agent to the patient. The subsequent acquisition may, for example, be obtained after a period of time to determine if injury has occurred during that period of time. The region of interest may include, for example, at least one of heart, blood, muscle, brain, nerve, skeletal, skeletal muscle, liver, kidney, lung, pancreas, endocrine, gastrointestinal and/or genitourinary tissue. A global characteristic of the region of interest of the first image and of the second image is determined so as to allow a comparison of the global characteristic of the first image and the second image to determine a potential for a change in global tissue characteristics such as may be caused, for example, by a global injury of the tissue of the region of interest. Such a comparison may include, for example, comparison of mean, average characteristics, histogram shape, such as skew and kurtosis, or distribution of intensities within the histogram.

In further embodiments of the present invention, the global characteristic is a characteristic of pixels/voxels of the region of interest that is based on substantially all of the pixels/voxels in the region of interest. The global characteristic may be an average intensity of pixels/voxels in the region of interest. The tissue in the region of interest may be at least one of cardiac tissue, brain tissue and/or nerve tissue. The first image and the second image may be magnetic resonance imaging (MRI) images.

While certain embodiments of the present invention are described herein with reference to the detection of global tissue characteristics, such as global injury in a patient, such as a human, additional embodiments of the present invention may include detection of global injury in vertebrate or invertebrate animals, reconstructed tissue and/or synthetic tissue. Accordingly, certain embodiments of the present invention should not be construed as limited to the detection of global injury in a human patient.

Particular embodiments of the present invention provide methods, systems and/or computer program products for detecting global cardiac injury in a patient. A first cardiac image is obtained after administration of a contrast agent to the patient. A second cardiac image is also obtained after administration of the contrast agent to the patient. A measure of intensity of the first cardiac image and a measure of intensity of the second cardiac image are determined and the measure of intensity of the first cardiac image and the measure of intensity of the second cardiac image are compared to determine a potential for a global cardiac injury. In certain embodiments of the present invention, an increase in the measure of intensity of the image indicates the possible presence of a global cardiac injury.

In further embodiments of the present invention, the first cardiac image and the second cardiac image are Magnetic Resonance Imaging (MRI) images and/or x-ray Computed Tomography (CT) images. Also, the measure of intensity of the first cardiac image and the measure of intensity of the second cardiac image may be average intensity of the respective images.

In additional embodiments of the present invention, a first image of a region of interest outside the heart corresponding to the first cardiac image is also obtained. Correction for variations in pixel intensity in normal myocardium tissue is performed on the first cardiac image using data from the first image of a region of interest outside the heart. Similarly, a second image of a region of interest outside the heart corresponding to the second cardiac image is obtained and correction for variations in pixel intensity in normal myocardium tissue is performed on the second cardiac image using data from the second image of a region of interest outside the heart. The measure of intensity of the first cardiac image and the measure of intensity of the second cardiac image are determined using the corrected first cardiac image with and the corrected second cardiac image. For example, the measure of increased brightness due to the present of contrast agent may be measured relative to normal myocardium tissue without contrast agent. The normal myocardium may not be suppressed to the same degree of darkness in all subjects and this variation may be accounted.

As will be appreciated by those of skill in the art in light of the present disclosure, embodiments of the present invention may be provided as methods, systems and/or computer program products.

BRIEF DESCRIPTION OF THE DRAWINGS

FIGS. 4A and 4B are flowcharts illustrating operations according to certain embodiments of the present invention;

DESCRIPTION OF EMBODIMENTS OF THE INVENTION

Figure 1:
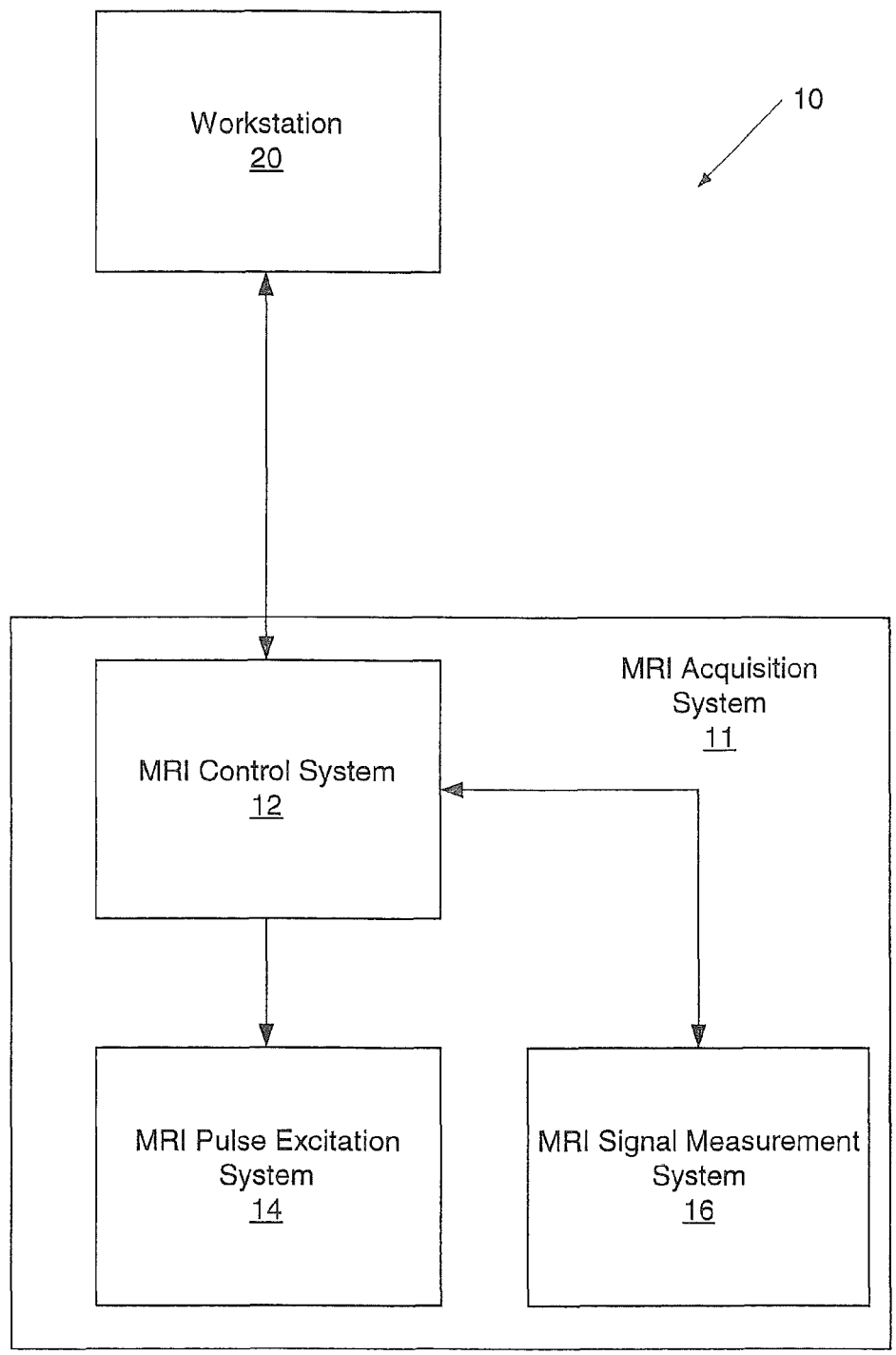
FIG. 1 is a block diagram of an MRI system according to embodiments of the present invention.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. Like numbers refer to like elements throughout. As used herein the team "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural fauns as well, unless the context clearly indicates otherwise. It will be further understood that the terms "comprises" and/or "comprising," when used in this specification; specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

As will be appreciated by one of skill in the art, the present invention may be embodied as methods, systems, or computer program products. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Furthermore, the user's computer, the remote computer, or both, may be integrated into other systems, such as an MRI system and/or X-Ray Computed Tomography system.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

MRI procedures are well established for identifying myocellular injury and LVEF in patients with ischemic cardiomyopathy secondary to coronary arteriosclerosis. Such procedures may identify localized cardiac injury. However, it is believed that such non-invasive imaging has not been utilized to identify global cardiac injury in patients with cardiomyopathy secondary to Chemotherapy administration. Early detection of myocellular injury could offer an opportunity to adjust medication dosages and reduce and/or minimize the cardio-toxic effects associated with chemotherapy. In this manner, maximal doses of chemotherapy could be administered to patients in the absence of myocellular injury and the desired effect of the chemotherapy medications may be more fully realized. While embodiments of the present invention may be particularly useful in doxorubicin therapy, embodiments of the present invention may also be utilized in other chemical therapies or regimens, and/or diagnostic environments where global cardiac injury is to be detected.

Embodiments of the present invention provide for detection of a change in tissue characteristics such as may result from an injury utilizing a comparison of a global characteristic of a region of interest in an image of the region of interest. A global characteristic of a region of interest is a characteristic of the region of interest that is based on one or more characteristics of all or substantially all of the pixels/voxels of the region of interest. Thus, in certain embodiments of the present invention, the global characteristic may be substantially independent of the location of pixels within the region of interest. Examples of a global characteristic may include but are not limited to a statistical analysis of a characteristic of pixels/voxels in the region of interest such as average intensity, a histogram of intensity values or other statistical analysis. The use of a comparison of global characteristics of images may allow for detection of injury where the pattern of injury is random and/or is not detectable at the resolution of the images that are compared. Embodiments of the present invention may also use global characteristics, not only to detect injury to an area, but also to detect abnormal accumulation of materials that are not found in their normal ratios within native tissue. Embodiments of the present invention may also be used with molecular imaging strategies, for example, directing the contrast with molecular recognition sites to areas of tissue and quantifying the presence of a target or molecular process. Thus, particular embodiments of the present invention may have application in detecting cancer, inflammation, infection, swelling or edema, scar tissue, etc. Also, embodiments of the present invention could be used to define metabolic pathways that are functioning within tissue in an organ system. Particular embodiments of the present invention provide for the detection of global cardiac injury utilizing non-invasive imaging after administration of a contrast agent. Non-invasive techniques suitable for use in embodiments of the present invention include Magnetic Resonance Imaging (MRI), ultrasound, x-ray computed tomography (CT), single photon emission computed tomography (SPECT) and/or positron emission tomography (PET). Comparisons may be made between a first or baseline image and a second image and the contrast of the image analyzed to detect the presence of global cardiac injury. As used herein, the term image refers to a spatial signal that may be evaluated to obtain a desired measure of signal intensity.

As used herein, the term "global injury" refers to a change in tissue composition and/or function that is in a substantially randomly distributed pattern and/or in a pattern that is not detectable at the resolution of the images that are analyzed to detect the injury. Thus, for example, "global cardiac injury" may refer to cardiac injury and/or replacement of native myocardial tissue with fibrous tissue, such as scar tissue, that results in necrosis and/or fibrosis in a substantially randomly distributed pattern and/or in a pattern that is not detectable at the resolution of the images that are analyzed to detect the injury. Global cardiac injury that may be detected by intensity analysis according to embodiments of the present invention may include, for example, viral cardiomyopathy, alcoholic cardiomyopathy, postpartum cardiomyopathy and/or idiopathic dilated cardiomyopathy. A global injury may also include disproportionate amounts of other abnormalities such as edema (extra fluid), fibrosis (scar tissue), etc. Thus, embodiments of the present invention may provide for the detection of global abnormal tissue.

Contrast agents suitable for use in embodiments of the present invention may include paramagnetic lanthanide chelates and/or paramagnetic lanthanide linked to a macromolecule, such as gadolinium DPTA. Other examples of MR contrast for perfusion imaging include the application of susceptibility agents containing iron oxide or dysprosium that introduce local inhomogeneity into the magnetic field by causing large fluctuations in the magnetic moment between blood and intracellular compartments. Imaging after the introduction of other drugs that induce cardiomyopathy, such as cocaine and/or alcohol could also be performed. These fluctuations result in the shortening of T2-star of neighboring hydrogen nuclei leading to loss of signal intensity. In particular embodiments of the present invention, the same contrast agent is utilized for each image.

Additionally, certain embodiments of the present invention may provide for contrast/intensity analysis without the administration of a contrast agent. For example, another example of perfusion imaging is the assessment of myocardial perfusion or injury without the administration of a contrast agent using a blood oxygen level dependent (BOLD) cardiac imaging via a T2-prepared true FISP, or 3D-T2-weighted sequence strategy. Other techniques use endogenous contrast including spin labeling and magnetization transfer contrast. Thus, in certain embodiments of the present invention, a global characteristic of a region of interest may be detected without the administration of a contrast agent.

An exemplary system 10 according to embodiments of the present invention is illustrated in FIG. 1. As seen in FIG. 1, an intensity analysis/MRI system 10 includes an MRI acquisition system 11 that may include an MRI control system circuit 12, an MRI pulse excitation system circuit 14 and an MRI signal measurement system circuit 16. The MRI control system circuit 12 controls operations of the MRI acquisition system 11 to obtain and provide MRI images during a cardiac cycle or portions thereof of a patient. The MRI control system circuit 12 may also assemble and transmit the acquired images to a workstation 20 or other such data processing system for further analysis and/or display. The workstation 20 may be in an MRI suite or may be remote from the MRI suite. The MRI pulse excitation system circuit 14 and the MRI signal measurement system circuit 16 are controlled to acquire MRI signals that may provide MRI images of the heart of a patient.

Conventional MRI systems, such as those provided by General Electric Medical Systems, Siemens, Philips, Varian, Broker, Marconi, Hitachi and Toshiba may be utilized to provide the desired MRI image frames collected after administration of a contrast agent.

While an exemplary intensity analysis/MRI system is illustrated in FIG. 1 and described herein with a particular division of functions and/or operations, as will be appreciated by those of skill in the art, other divisions of functions and/or operations may be utilized while still benefiting from the teachings of the present invention. For example, the MRI control system circuit 12 could be combined with either the MRI pulse excitation system circuit 14 or the MRI signal measurement system circuit 16. Thus, the present invention should not be construed as limited to a particular architecture or division of MRI functions/operations but is intended to cover any architecture or division of functions/operations capable of carrying out the operations described herein.

Figure 2:
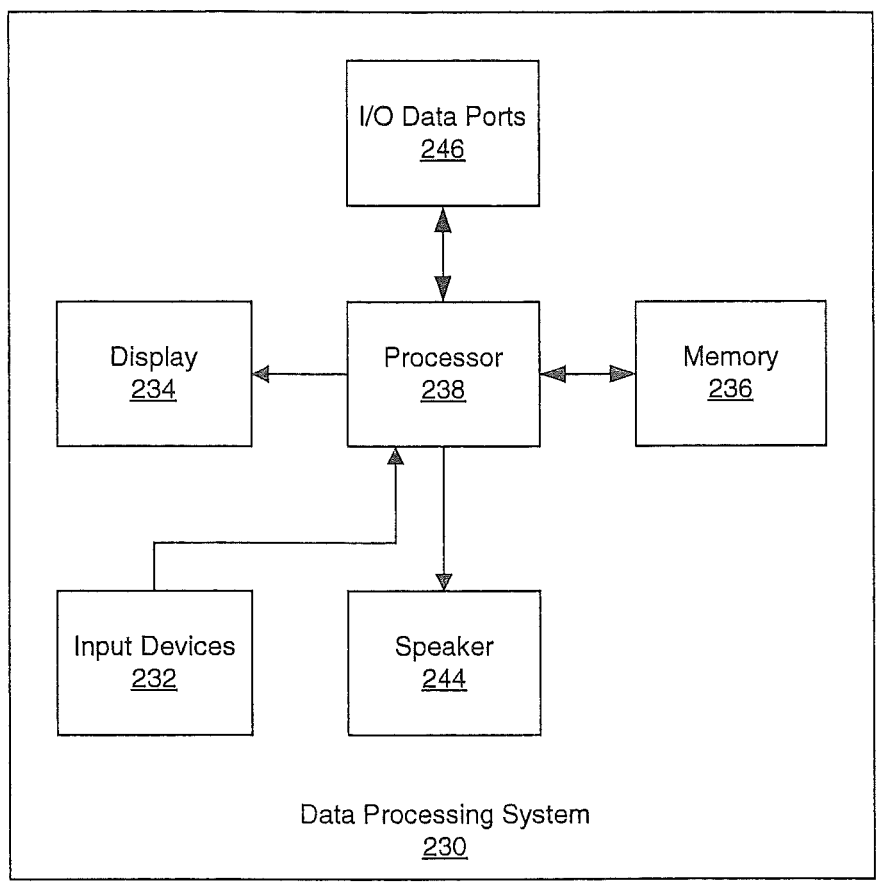
FIG. 2 is a block diagram of a data processing system according to embodiments of the present invention.

FIG. 2 illustrates an exemplary embodiment of a data processing system 230 suitable for providing a workstation 20 and/or MRI control system circuit 12 in accordance with embodiments of the present invention. The data processing system 230 typically includes input device(s) 232 such as a keyboard or keypad, a display 234, and a memory 236 that communicate with a processor 238. The data processing system 230 may further include a speaker 244, and an I/O data port(s) 246 that also communicate with the processor 238. The I/O data ports 246 can be used to transfer information between the data processing system 230 and another computer system or a network. These components may be convention-al components such as those used in many conventional data processing systems that may be configured to operate as described herein.

Figure 3:
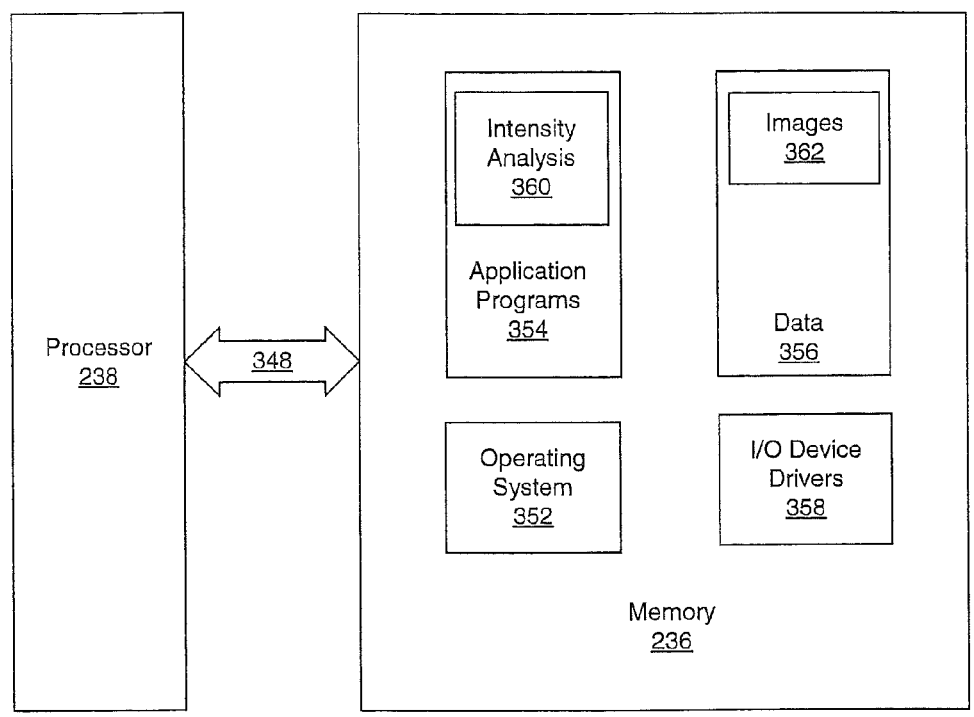
FIG. 3 is a block diagram of a data processing system according to embodiments of the present invention.

FIG. 3 is a block diagram of embodiments of data processing systems that illustrates systems, methods, and computer program products in accordance with embodiments of the present invention. The processor 238 communicates with the memory 236 via an address/data bus 348. The processor 238 can be any commercially available or custom microprocessor. The memory 236 is representative of the overall hierarchy of memory devices containing the software and data used to implement the functionality of the data processing system 230. The memory 236 can include, but is not limited to, the following types of devices: cache, ROM, PROM, EPROM, EEPROM, flash memory, SRAM, and DRAM.

As shown in FIG. 3, the memory 236 may include several categories of software and/or data used in the data processing system 230: the operating system 352; the application programs 354; the input/output (I/O) device drivers 358; and the data 356. As will be appreciated by those of skill in the art, the operating system 352 may be any operating system suitable for use with a data processing system, such as OS/2, AIX or System390 from International Business Machines Corporation, Armonk, N.Y., Windows95, Windows98, Windows2000, WindowsNT or WindowsXP from Microsoft Corporation, Redmond, Wash., Unix or Linux. The operating systems may be configured to support an TCP/IP-based or other such network communication protocol connection. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 230 and preferably include at least one application that supports operations according to embodiments of the present invention. Finally, the data 356 represents the static and dynamic data used by the application programs 354, the operating system 352, the I/O device drivers 358, and other software programs that may reside in the memory 236.

As is further seen in FIG. 3, the application programs 354 may include a intensity analysis application 360. The intensity analysis application 360 may carry out the operations described herein for evaluating images to detect changes in intensity that may be associated with global cardiac injury. The data portion 356 of memory 236, as shown in the embodiments of FIG. 3, may include image data 362, such as MRI image data that includes first and second images of tissue of a region of interest for comparison.

While the present invention is illustrated, for example, with reference to the intensity analysis application 360 being an application program in FIG. 3, as will be appreciated by those of skill in the art, other configurations may also be utilized while still benefiting from the teachings of the present invention. For example, the intensity analysis application 360 may also be incorporated into the operating system 352, the I/O device drivers 358 or other such logical division of the data processing system 230. Thus, the present invention should not be construed as limited to the configuration of FIG. 3 but is intended to encompass any configuration capable of carrying out the operations described herein.

FIG. 4A illustrates operations according to particular embodiments of the present invention. As seen in FIG. 4A, a first image of a region of interest of tissue of a patient is obtained (block 400). An image may be obtained, for example, by acquisition of the image from an imaging system, such as the imaging systems discussed above, and/or by obtaining the image from a database, file or other storage of the image data. For example, a patient's images may be maintained in a historical database for subsequent recall as a first image for comparison. The region of interest of tissue in a patient that is imaged may, for example, include heart, blood, muscle, brain, nerve, skeletal, skeletal muscle, liver, kidney, lung, pancreas, endocrine, gastrointestinal and/or genitourinary tissue. In particular embodiments of the present invention, the tissue may be human tissue, In other embodiments, the tissue may be animal tissue.

As is further illustrated in FIG. 4A, a second image of the tissue in the region of interest for comparison to the first image is obtained after a period of time, such as hours, days, weeks, months or even years (block 402). The second image for comparison reflects any change in the characteristics of the tissue in the region of interest. The second, comparison image may be acquired and registered (taken at the same slice locations) with the corresponding first image. The second image may also be obtained as described above with reference to the first image. Thus, for example, comparison images may be historical images as well as recently acquired images.

The first image and the second image are evaluated to determine one or more global characteristics of the images (block 404). The global characteristic of the images may, for example, be an average intensity of pixels/voxels in the region of interest. The global characteristic could also be a statistical analysis of the pixels/voxels in the region of interest. For example, the standard deviation, mean value or other statistical analysis of the pixels/voxels in the region of interest could be determined. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

The results of this evaluation are provided to a user or may be provided for further analysis (block 406). For example, a comparison of the first image and the second image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface.

The results of the evaluation of the global characteristic of the image of the tissue in the region of interest may be utilized in the detection, perhaps the early detection, of change in tissue characteristics such as may result, for example, from injury to the tissue or other conditions as discussed above. Such a global characteristic evaluation may be suitable in detecting tissue characteristics that result in a random pattern of different tissue characteristics in the region of interest or that are imaged at a resolution where a pattern of the tissue characteristic cannot be detected.

FIG. 4B illustrates operations according to particular embodiments of the present invention utilizing administration of a contrast agent. As seen in FIG. 4B, a baseline image of a region of interest of tissue of a patient is obtained (block 450). An image may be obtained, for example, by acquisition of the image from an imaging system, such as the MRI system illustrated in FIG. 1, and/or by obtaining the image from a database, file or other storage of the image data. For example, a patient's images may be maintained in a historical database for subsequent recall as a baseline image for comparison. The baseline image may be an image taken without administration of a contrast agent, after administration of a contrast agent and/or a period of time, such as twenty minutes, after administration of the contrast agent. The region of interest of tissue in a patient that is imaged may, for example, include heart, blood, muscle, brain, nerve, skeletal, skeletal muscle, liver, kidney, lung, pancreas, endocrine, gastrointestinal and/or genitourinary tissue. In particular embodiments of the present invention, the tissue may be human tissue. In other embodiments, the tissue may be animal tissue.

As is further illustrated in FIG. 4B, an image of the tissue in the region of interest for comparison to the baseline image is obtained after administration of a contrast agent (block 452). The image for comparison reflects the effect of the contrast agent on the tissue in the region of interest. In particular embodiments of the present invention, the image may be a myocardial delayed enhancement (MDE) image. The comparison image may be acquired and registered (taken at the same slice locations) with the corresponding baseline image. The comparison image may also be obtained as described above with reference to the baseline image. Thus, for example, comparison images may be historical images as well as recently acquired images.

The baseline image and the comparison image are evaluated to determine one or more global characteristics of the images (block 454). The global characteristic of the images may, for example, be an average intensity of pixels/voxels in the region of interest. The global characteristic could also be a statistical analysis of the pixels/voxels in the region of interest. For example, the standard deviation, mean value or other statistical analysis of the pixels/voxels in the region of interest could be determined. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

The results of this evaluation are provided to a user or may be provided for further analysis (block 456). For example, a comparison of the baseline image and the comparison image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface The results of the evaluation of the global characteristic of the image of the tissue in the region of interest may be utilized in the detection, perhaps the early detection, of injury to the tissue. Such detection may be provided for injuries that result in a different concentration of contrast agent being present in injured versus healthy tissue. Such a global characteristic evaluation may be suitable in detecting injuries that result in a random pattern of injured tissue in the region of interest or that are imaged at a resolution where a pattern of the injured tissue cannot be detected. Thus, for example, with a 1.5 Tesla MRI imaging system, a typical myocardial infarct would not be considered a global image and the detection and location of increased intensity in an image in the location of the infarct would not be considered a random pattern of injured tissue or a pattern of injured tissue that could not be detected at the resolution of the MRI imaging system.

Figure 5:
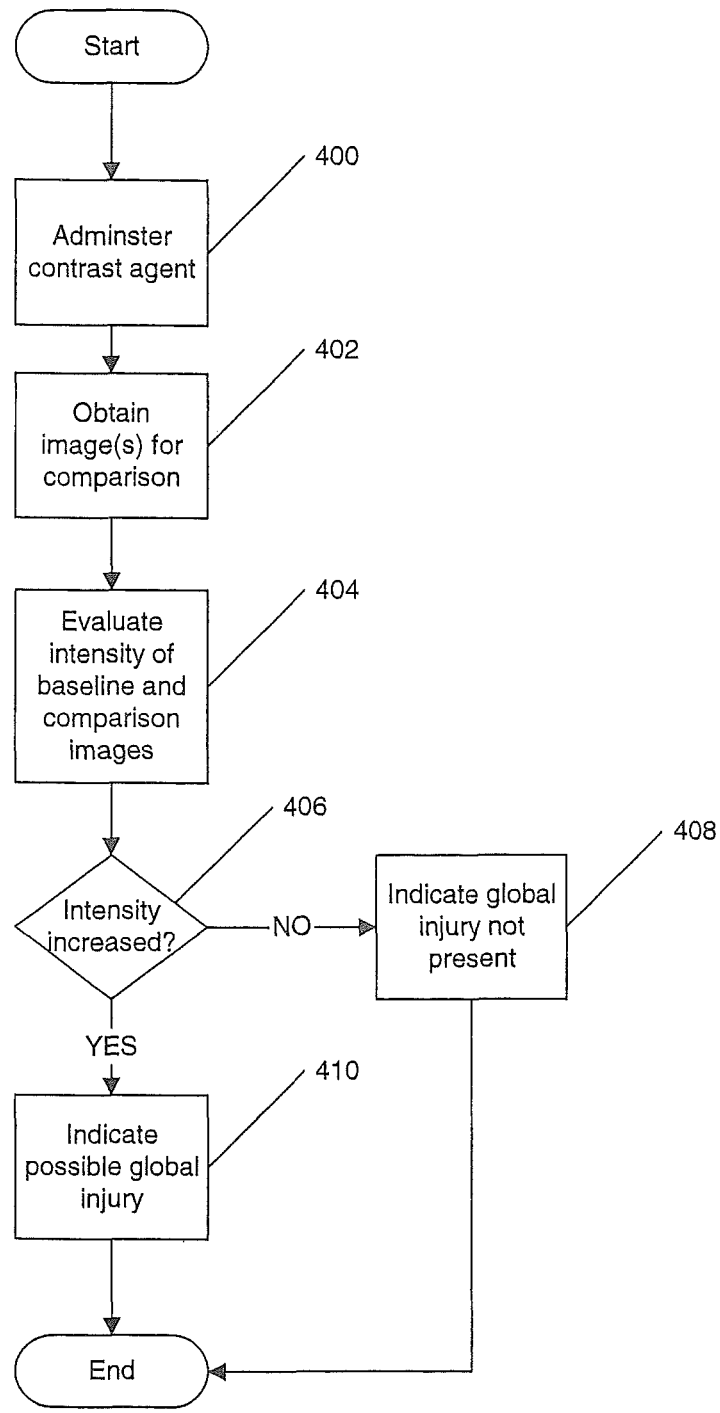
FIG. 5 is a flowchart illustrating operations according to certain embodiments of the present invention.

FIG. 5 illustrates operations according to particular embodiments of the present invention. As seen in FIG. 5, a contrast agent is administered to a patient (block 400) and an image of at least a portion of the patient's heart is acquired (block 402). In particular embodiments of the present invention, the acquired perfusion image may be a myocardial delayed enhancement (MDE) image. In MDE, 20 minutes after a contrast agent, such as gadolinium DPTA, is administered, some of it has leaked into necrotic (dead) tissue and will appear bright (hence, delayed enhancement). These images may be acquired and registered (taken at the same slice locations) with the corresponding baseline perfusion images.

The acquired image is evaluated and the intensity of the image is compared to a baseline image (block 404). The baseline image is an image of the patient's heart and may be a previously acquired image that was also acquired after administration of a contrast agent. The baseline image may have been acquired prior to administration of a treatment regimen or may be an image acquired at an earlier evaluation. The comparison of images may be a comparison of average intensity of the images as discussed in more detail below. If the intensity of the image has not increased in comparison to the baseline image (block 406), then an indication that a global cardiac injury is not present may be provided (block 408). If the intensity of the image has increased in comparison to the baseline image (block 406), then an indication that a global cardiac injury may be present may be provided (block 410).

In still further embodiments of the present invention, the evaluation of global image characteristics, such as the intensity of the cardiac images, may be performed automatically or partially automatically utilizing image processing techniques. An automatic comparison may, for example, also include registration of the differing images to each other. Such a registration may be provided utilizing conventional pattern recognition and/or alignment techniques such that corresponding pixels of the images or portions of the images are each associated with approximately the same physical location within the patient.

In particular embodiments of the present invention, a patient may be taken to the MRI suite where they will be placed supine on the MRI table and ECG leads and respiratory gating bellows applied. MRI scans may be performed on, for example, a 1.5 Tesla GE $CV_i$ scanner with a phased array surface coil applied around the chest to optimize signal to noise or other MRI scanner. Images may be acquired using a fast gradient echo technique, with the repetition time (TR) and echo time (TE) based on the R-R interval of the subject. Multislice coronal, gradient echo sequences may be used to obtain scout images of the chest and locate the left ventricle. Subjects may be injected intravenously with a gadolinium contrast agent (0.2 mmole/kg Gadoteridol (Prohance, Bracco Diagnostics, Princeton, N.J.). The time of this injection may be recorded.

About twenty minutes from the time of the contrast injection, three short axis views (basal, middle, and apical) delayed enhancement images may be acquired using a fast gradient echo preceded by a nonselective saturation pulse. Landmarks for these acquisitions may be measured off of the coronary sinus within the atrio-ventricular groove extending horizontally across the mitral valve annulus. These images may be acquired using a 38 cm field of view, 24 views per segment, 8 mm slice thickness, 2 NEX, 256×256 imaging matrix, and a 0.75 rectangular field of view. The inversion time (TI) for the delayed enhancement images may be adjusted 140 to 160 msec to provide a uniform dark background. Additionally, in these three short axis slice positions, a fast-gradient-recalled echo pulse sequence may be used with phase-encode ordering. These images may be subjected to phase-sensitive reconstruction that reduces the variation in apparent contrast intensity that is observed in the magnitude images as TI is changed. In addition, the phase-sensitive reconstruction may decrease the sensitivity to changes in tissue $T_1$ with increasing delay from the Gadolinium contrast injection.

Upon completion of the image acquisition, the locations, measurements, and representative images may be transferred electronically to a database. This information may be available to the MRI technologist via a PC workstation at the time of each scan and facilitate the relocation of slice positions (registration) on subsequent studies.

Figure 12:
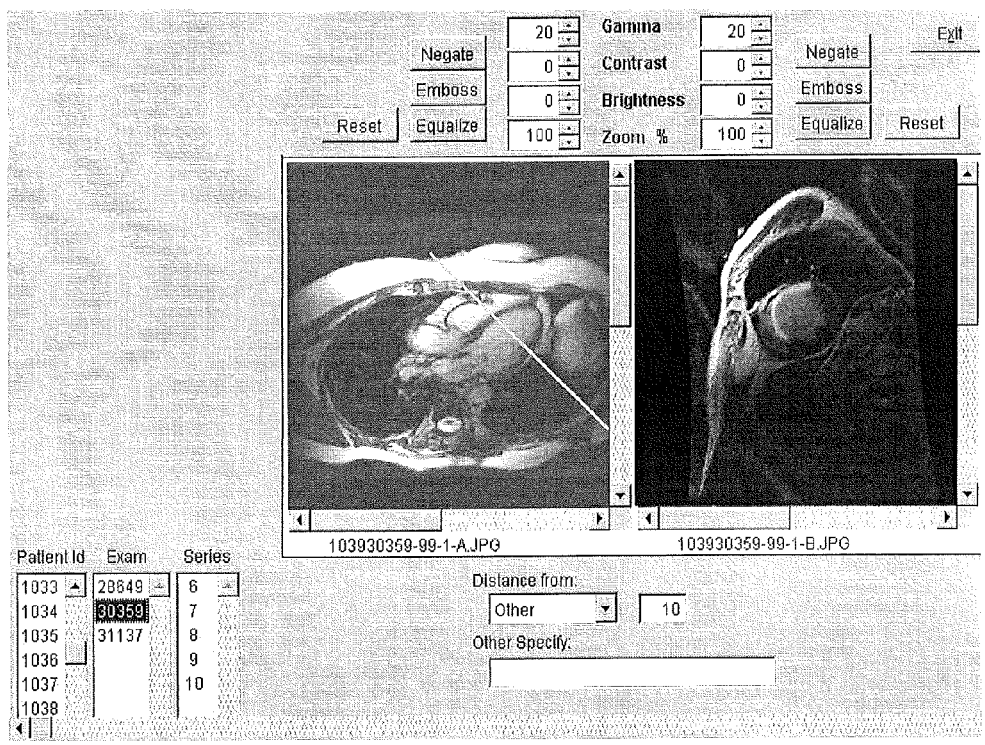
FIG. 12 is a screen capture of image planning software for reproducing slice positions.

FIG. 12 illustrates a screen capture of software for planning image slices. Such software may provide electronic copies of image planning slices and positioning coordinates that are saved for retrieval during subsequent visits in a study. This has the effect of improving the ability of the MRI technologist to reproduce slice positions from the previous visits. In the example of FIG. 12, a long-axis view of the heart with a resultant delayed enhancement short axis view is shown.

On the delayed enhancement acquisitions, regions of interest (ROIs) encompassing the LV myocardium on all of the multi-slice acquisitions may be determined. High signal intensities associated with the blood pool within the LV cavity may be avoided. The signal intensity and location (x, y, and z coordinates) of each (or selected) voxel within the ROI's may be recorded from both baseline and delayed enhancement images. Values may also be derived from subtracting the mean intensity for a separate ROI, for example, without contrast agent, from the intensities by using a separate ROI within the air/space outside of the body. The ROI's may be utilized as discussed below in the Examples in determining a change in intensity between two images.

While embodiments of the present invention have been described above with respect to particular views, regions, areas and/or slices of the heart, other views, regions, areas and/or slices of the heart may also be utilized. Furthermore, fewer or greater than three slices may be utilized. Additionally, the images may be taken along the long or short axis of the heart. Accordingly, certain embodiments of the present invention should not be construed as limited to the particular views of the heart but may include any view and/or number of views of the heart that allow for intensity analysis to detect global cardiac injury.

Typically, a first baseline image will be obtained prior to or early in treatment or as an initial reference point in diagnosis of change in cardiac condition. Subsequent images for comparison may be taken daily, weekly or at other fixed or variable interval(s) or prior to or after planned treatment, such as a cytotoxic treatment.

The invention will now be described in more detail in the following non-limiting examples.

EXAMPLES

As briefly mentioned above, conventionally, identification of myocellular necrosis in patients with an ischemic cardiomyopathy has been performed by locating the voxels with a signal intensity >2 standard deviations above the background intensity within non-enhanced LV myocardium. The amount of necrosis is quantified by determining the transmural extent of hyperenhancement expressed as a ratio of the number of high intensity pixels extending linearly from the endocardial to the epicardial surface relative to the total distance from the endocardium to epicardium. Since myocardial necrosis proceeds in a wavefront from the endocardial to epicardial surface in the setting of reduced coronary arterial blood flow, this method is useful for assessing the amount of necrosis after myocardial infarction.

Figure 6:
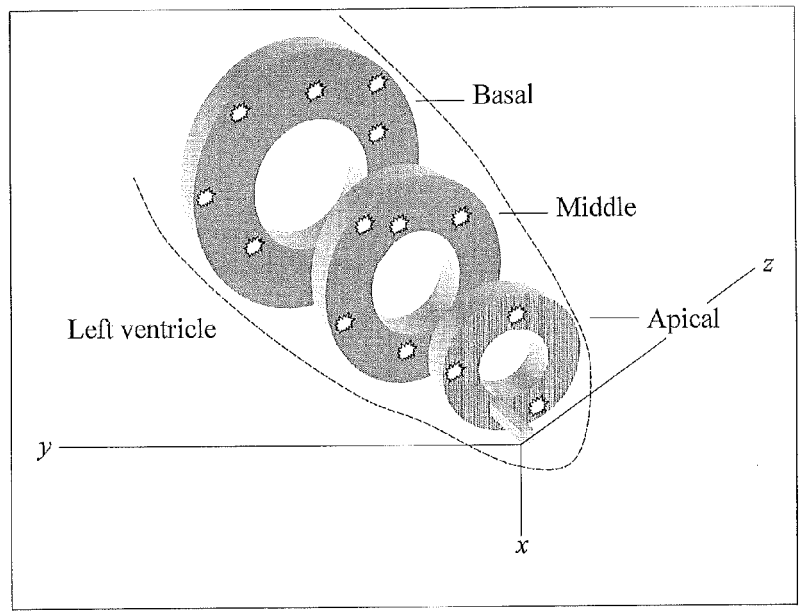
FIG. 6 is a 3-Dimensional depiction of three short axis planes of a left ventricle.

However, this method may not be as well suited for a process that causes necrosis to susceptible tissue throughout the LV myocardium in a randomly distributed pattern (e.g. a global injury). To overcome this limitation, voxels, and in some embodiments all the voxels, within three short axis slice positions (apex, middle, and base) within the LV may be sampled and the intensity, x, y, and z coordinates of each voxel identified in 3-dimensional space (FIG. 6). FIG. 6 is a 3-Dimensional depiction of 3 short axis (basal, middle, and apical) planes of the left ventricle. In each plane, the grid of small boxes on the face of each slice demarcate the voxels. During analysis, the image intensity of each voxel and the x, y, and z coordinates are recorded. In this way, high intensity pixels identified with the delayed enhancement technique associated with a randomly distributed process causing myocellular necrosis (white splotches on images) can be characterized.

Correction for variations in the intensity of voxels in the images may also be identified by determining the intensity of voxels within a target region, typically, a 1 cm diameter circular region of interest (ROI) placed outside the heart. For each apical, middle, and basal slice, the number of pixels at a given intensity may be determined and the intensity from the ROI external to the heart subtracted from the pixels. In certain embodiments, for each slice, the mean intensity of all voxels and the peak voxel intensity in the highest 40% of the distribution may be determined (FIG. 6). In this way, regions of high intensity pixels may be identified relative to their location within the left ventricle.

Figure 7:
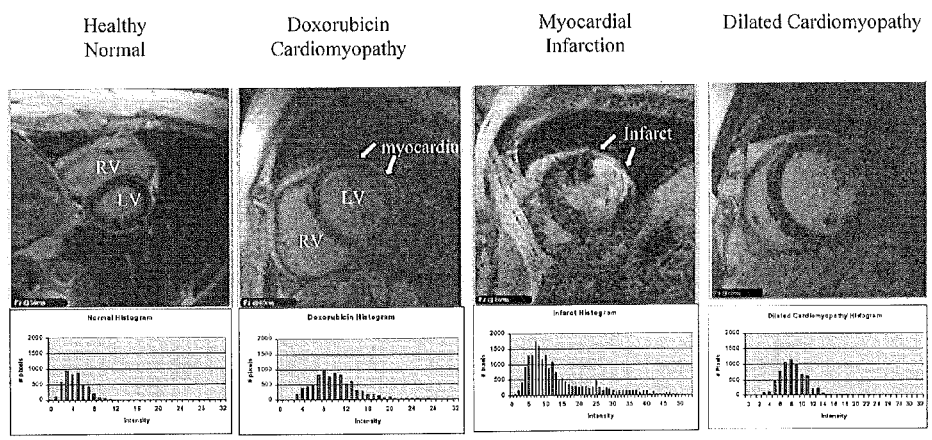
FIG. 7 are delayed enhancement MRI images in a middle (mid-plane) short axis view of the left ventricle with corresponding intensity histograms.

FIG. 7 are exemplary delayed enhancement MR images (top panels) in a middle short axis view of the LV. The myocardium is gray and the blood pool is white. The number (y-axis) and intensity (x-axis) of voxels within the ROI (redline) 20 minutes after contrast administration are displayed in the bottom panels. The contrast is taken up by all myocytes, but 20 minutes after administration, it is not cleared from necrotic cells. As shown, the mean intensity of contrast uptake is low in the healthy normal patient (far left) and highest in the patient with an infarct (third from left). An intermediate mean intensity is displayed on the histogram associated with the Doxorubicin cardiomyopathy patient (second from left).

To determine the utility of MRI assessments of the location and magnitude of gadolinium contrast uptake 20 minutes after intravenous administration, a cross-sectional study in 4 groups of age (range 35 to 50 years) and gender matched participants was performed. These included:

a) (Group I): 4 subjects (1M,3F) without medical illness, taking no cardiac medications, and with normal LV systolic and diastolic function by MRI, b) (Group II): 3 patients (3F) without coronary arterial luminal narrowings on contrast coronary angiography but with poor LV ejection fraction (<35%) and congestive heart failure secondary to Doxorubicin administration, c) (Group III): 3 patients (2M,1F) without coronary arterial luminal narrowings on contrast coronary angiography and with poor LV ejection fraction (<35%) and congestive heart failure secondary to an idiopathic dilated cardiomyopathy, and d) (Group IV): 3 patients (2M,1F) with LV dysfunction secondary to an ischemic cardiomyopathy and prior ST-segment elevation myocardial infarction.

Figure 8:
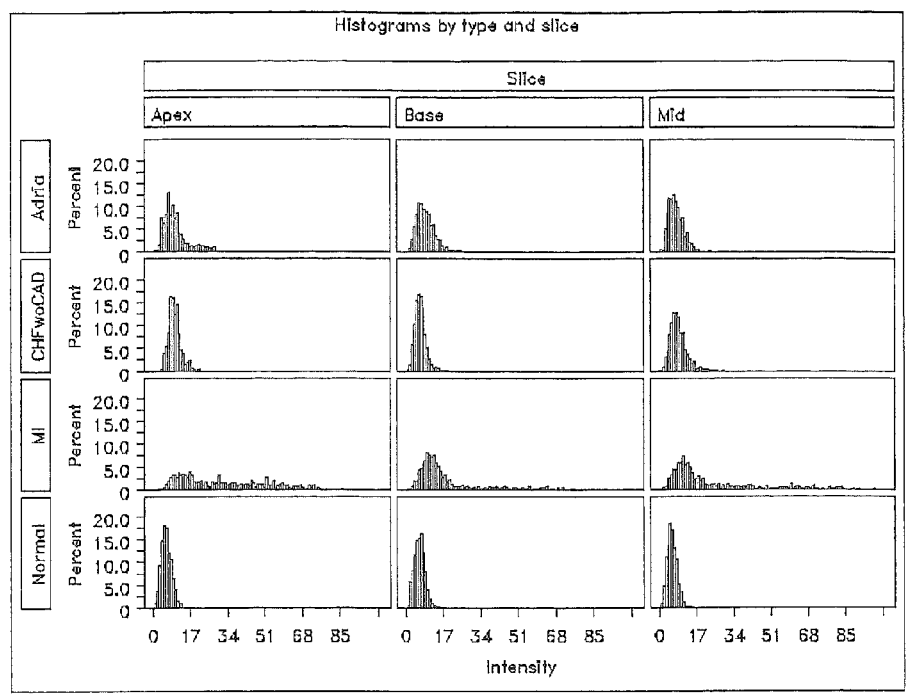
FIG. 8 are intensity histograms of voxels within a region of interest (ROI)

A middle short axis image and the distribution of intensities of voxels within the image from one subject in each group is displayed in FIG. 7, and the distributions of voxel intensities within all of the slices from all of the participants are displayed in FIG. 8.

In FIG. 8, the percentage (y-axis) and intensity (x-axis) of voxels within ROIs from all participants in the cross-sectional sampling of subjects 20 minutes after contrast administration.

As displayed in FIG. 7, an increased percentage of intensities in the 15 to 30 range are displayed in patients with cardiomyopathy due to chemotherapy administration compared to normal age matched controls. This pattern of intensities appears different from that seen in patients with an ischemic cardiomyopathy.

To determine the relationship between the pattern of high intensity pixels within each slice of the left ventricle, an auto-correlation statistic was used. The serial auto-correlation measure (I) is defined as follows. Let $\delta_{ij}$ be a weighting function of the distance between pixels i and j, n be the number of pixels, and $x_i$ be the intensity for the $i^{th}$ pixel. Then define $$I = n \frac{\sum_{ij} \delta_{ij}(x_i - \bar{x})(x_j - \bar{x})}{\left(\sum_{ij} \delta_{ij}\right)\left(\sum_i (x_i - \bar{x})^2\right)}.$$

I is a measure of serial autocorrelation and is higher when adjacent pixels are both higher or lower than the mean (Ripley, 1981). In practice, the expression $$\delta_{ij} = \exp\left(-\frac{1}{2}d(x_i, x_j)\right)$$

has been used, where $d(x_i,x_j)$ is the Euclidian distance between points $x_i$ and $x_j$.

Figure 9:
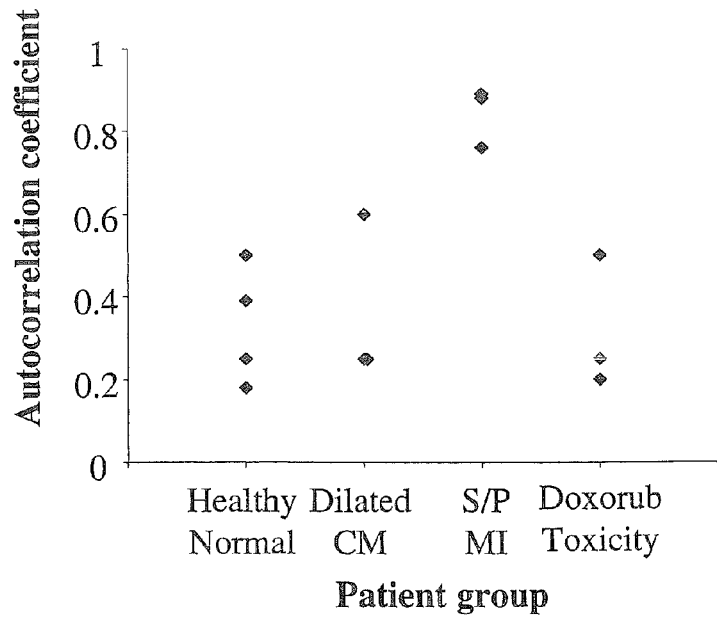
FIG. 9 is a graph of auto-correlation measures for study patients.

Using this form of analysis a high number indicates pattern clustering within the ROI, and a low number is more indicative of a random association. As shown in FIG. 9, the heightened signal intensities associated with MI were tightly clustered in the infarct zone; whereas those associated with Doxorubicin toxicity were scattered throughout the LV. The pattern of contrast uptake within the LV in patients with cardiomyopathy secondary to Doxorubicin administration was random and significantly different (p<0.001) from the pattern of high signal intensity voxels associated with myocardial necrosis secondary to myocardial infarction.

To determine if contrast enhancement is associated with a fall in LVEF in individuals receiving chemotherapy, a baseline MRI examination was performed in patients prior to initiation of chemotherapy and then additional MRI examinations were performed according to the research study protocol. Echocardiography exams were also performed to monitor patient left ventricular function between MRI examinations. One subject had developed dyspnea and received a echocardiogram to determine LVEF. The subject had a fall in LVEF from 55% to 48%. This individual underwent MRI testing and image analysis. The image analysis of this subject was compared to one other subject who had not developed a drop in LVEF during course of chemotherapy regimen. Images and the voxel intensities in the middle short axis view from the patients are displayed in FIG. 10.

Figure 10:
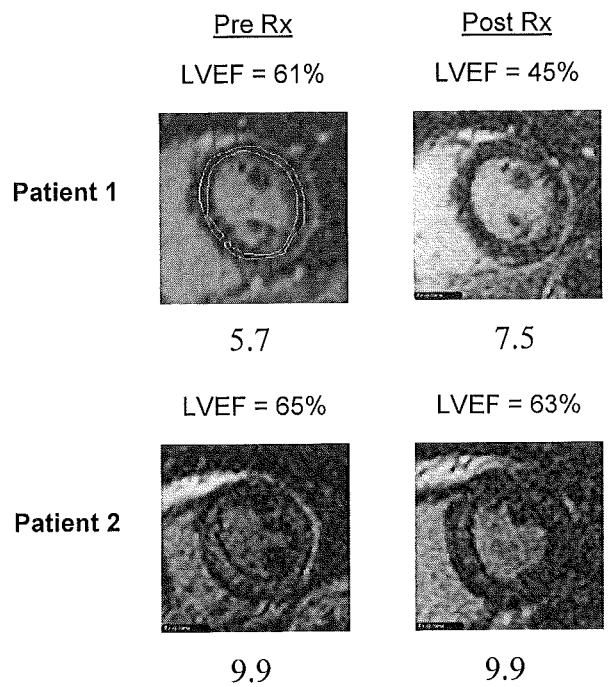
FIG. 10 are images and mean voxel intensities for two separate patients.

FIG. 10 illustrates images and mean voxel intensities at two time points in two separate patients while receiving chemotherapy, one of which developed dyspnea during the course of chemotherapy. Pre-treatment images in both patients are displayed on the left and post treatment images are displayed on the right. Mean voxel intensities for the ROI within the image are displayed under the image. In patient 1 that developed a fall in LVEF (Top panels), heightened contrast uptake and signal intensity occurred in the second exam after receipt of 400 mg/m² of anthracyclines for treatment of breast cancer. In the second patient (Bottom panels), no fall in LVEF occurred and the uptake pattern showed no significant change. As shown, in the individual with a fall in LVEF, there was a significant increase in the intensity of voxels within the LV in the second exam compared to the first, whereas in the individual without a fall in LVEF, there was no marked change on the second exam.

Figure 11:
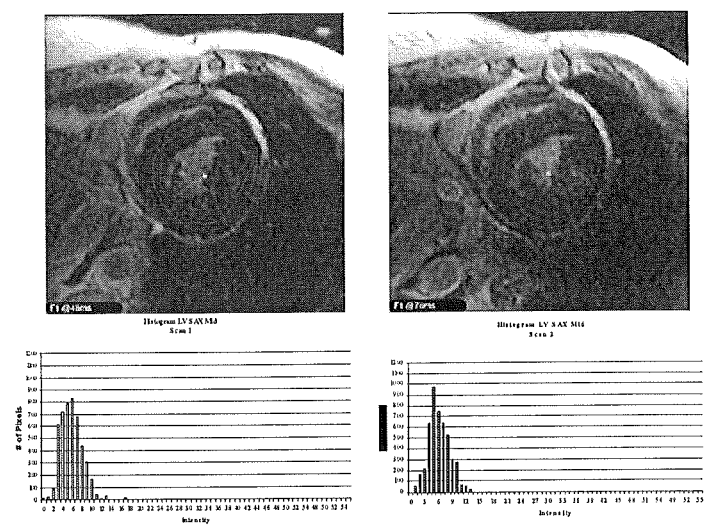
FIG. 11 are middle short axis views acquired twenty-one days apart for a patient.

To determine the variance of MRI delayed enhancement voxel intensities over time in participants without a substantive change in their medical condition, four individuals were studied twice after contrast administration over a two week period. Images from one of the participants are shown in FIG. 11, and data from both sample points in all four individuals is shown in Table 1.

TABLE 1

In four participants, MRI intensity (mean ± standard deviation) and LVEF.

|  | Day 1 | Day 21 |  |
| --- | --- | --- | --- |
| LVEF | 0.67 ± 0.04 | 0.64 ± 0.04 | p = NS |
| Mean intensity | 6.64 ± 1.15 | 6.60 ± 0.96 | p = NS |

FIG. 11 illustrates middle left ventricular short axis views acquired 21 days apart in an individual without a change in their condition. Note the near exact replication of the slice position on the second acquisition using software discussed elsewhere herein. Twenty minutes after contrast administration, the signal intensity within the ROIs was not significantly different, 5.8 versus 6.1 (p=NS). MRI examinations with this technique may be acquired reproducibly over time.

There was little change in the uptake patterns of contrast in the subjects between the first and second exam, and for the four individuals measured at two points in time, the correlation between the 2 measurements was excellent (y=0.87x+1.2, $R^2$=0.96).

Based on the above data, it appears that delayed enhancement MRI uptake patterns of contrast are elevated in patients with cardiomyopathy secondary to chemotherapy induced cardiotoxicity compared to age and gender matched control subjects. The pattern of this contrast uptake is diffuse and randomly distributed throughout the left ventricle in a fashion that is distinctly different from myocellular injury observed in patients sustaining a myocardial infarction. In the project involving two patients receiving chemotherapy, heightened contrast uptake occurred coincident with a fall in LVEF in one, but not the other that did not develop a fall in LVEF. Such a methodology and analysis methods may be highly reproducible and exhibit low intraobserver variability.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims.

That which is claimed is:

1. A method of evaluating tissue characteristics in a patient, comprising:
electronically applying a statistical autocorrelation analysis to image data to determine a pattern of at least one pixel parameter within a three dimensional tissue volume of a region of interest to evaluate whether the pattern is (i) clustered or (ii) distributed or diffuse; and determining a potential of a global injury, global abnormal tissue, or global abnormal accumulation of materials not found in normal ratios within native tissue based on the determined pattern, wherein the global injury, global abnormal tissue, and/or global abnormal accumulation is due to a change in tissue composition and/or function that is in a diffuse and/or distributed pattern in the region of interest, wherein the electronically applying is carried out using at least one processor.

2. The method of claim 1, wherein the statistical autocorrelation analysis is carried out using an autocorrelation statistic, wherein the image data is derived from cardiac MRI images, and wherein the determining the potential is carried out to determine the potential of a future onset of global cardiac injury.

3. The method of claim 1, wherein the determining the potential is carried out electronically to determine the potential of a global cardiac injury by analyzing cardiac MRI image data using the at least one processor and is carried out to determine the potential of global injury associated with at least one of viral cardiomyopathy, alcoholic cardiomyopathy, postpartum cardiomyopathy, idiopathic dilated cardiomyopathy, cardiac necrosis, inflammation, infection, cardiac edema or cardiac fibrosis.

4. The method of claim 2, wherein the determining step is carried out electronically, the method further comprising electronically displaying the determined potential of the future onset of global cardiac injury to a workstation having a display associated with a clinician or other user.

5. The method of claim 1, wherein the image data comprises at least three short axis cardiac MRI slices of a left ventricle, wherein the at least one pixel parameter is signal intensity, and wherein the applying the autocorrelation is carried out to evaluate whether heightened signal intensities are associated with myocardial infarction based or whether the heightened signal intensities are tightly clustered in an infarct zone or whether heightened signal intensities are distributed through the left ventricle so as to be associated with the global injury, global abnormal tissue, and/or global abnormal accumulation.

6. The method of claim 1, wherein the three dimensional tissue volume of the region of interest comprises cardiac tissue and the image data comprises MRI cardiac image data, and wherein the applying the autocorrelation analysis comprises an autocorrelation statistic number (I), with a respective clustered pattern indicated by an autocorrelation statistic number different than that associated with a respective distributed pattern.

7. The method of claim 1, wherein the statistical autocorrelation analysis is carried out using an autocorrelation statistic, and wherein the at least one pixel parameter includes MRI signal intensity.

8. The method of claim 1, wherein the statistical autocorrelation analysis is carried out using an autocorrelation statistic, and wherein the at least one pixel parameter includes color saturation of MRI image data.

9. The method of claim 1, wherein the statistical autocorrelation analysis is carried out using an autocorrelation statistic, and wherein the image data comprises MRI image data, and wherein the at least one pixel parameter includes a relative characteristic of multiple pixels/voxels.

10. The method of claim 9, wherein the relative characteristic includes contrast ratios.

11. The method of claim 1, wherein the image data is derived from at least one MRI image taken after administration of a cytotoxic drug to the patient.

12. The method of claim 1, wherein the statistical autocorrelation analysis is carried out using an autocorrelation statistic, and wherein the region of interest is the heart, and wherein the image data is derived from MRI perfusion image slices or are from MRI images acquired using blood oxygenation level dependent (BOLD) cardiac imaging.

13. The method of claim 1, wherein the image data comprises cardiac MRI image data, wherein the statistical autocorrelation analysis is carried out using an autocorrelation statistic, and wherein the global injury, global abnormal tissue or global accumulation is associated with at least one of cardiomyopathy, cardiac edema, inflammation, infection or cardiac fibrosis.

14. The method of claim 1, wherein the image data is associated with first and second images obtained at intervals prior to or after delivery of a planned cancer therapy, and wherein the determining the potential is carried out to evaluate whether myocellular necrosis is likely to result in a drop in LVEF (left ventricular ejection fraction).

15. The method of claim 14, wherein the determining the autocorrelation analysis is carried out electronically to determine whether a distribution pattern of voxels or pixels of high intensity in a left ventricle myocardium is distributed rather than clustered to predict whether a myocellular injury secondary to a cancer therapy is likely to be associated with a fall in LVEF (left ventricular ejection fraction).

16. The method of claim 1, wherein the image data comprises MRI image data, and wherein the determining the potential is carried out electronically by assessing the pattern of the at least one pixel parameter in image data of myocardial perfusion and/or injury obtained without administration of a contrast agent.

17. A system for evaluating tissue characteristics in a patient, comprising:
at least one processor configured to: (i) apply an autocorrelation to a three dimensional tissue volume of a region of interest in at least one patient image to evaluate whether at least one defined pixel/voxel characteristic is (a) clustered or (b) distributed or diffuse: and (ii) determine if there is a potential of a global injury, global abnormal tissue, or global abnormal accumulation of materials not found in normal ratios within native tissue based on whether the pixel/voxel characteristic is distributed rather than clustered.

18. The system of claim 17, wherein the patient image comprises cardiac MRI images taken at different points of time, wherein the at least one processor is configured to determine a potential for a future onset of global cardiac injury as the potential of the global injury.

19. The system of claim 17, wherein the at least one processor is configured to determine the potential of the future onset of the global cardiac injury associated with at least one of viral cardiomyopathy, alcoholic cardiomyopathy, postpartum cardiomyopathy, idiopathic dilated cardiomyopathy, cardiac necrosis, cardiac edema or cardiac fibrosis.

20. The system of claim 17, further comprising a display in communication with the at least one processor configured to display the potential of the future onset of global cardiac injury.

21. The system of claim 17, wherein the at least one image comprises image data from three short axis cardiac MRI slices of a left ventricle, wherein the at least one defined pixel/voxel characteristic comprises signal intensity, and wherein the autocorrelation is carried out to evaluate whether heightened signal intensities are associated with myocardial infarction based on whether the heightened signal intensities are tightly clustered in an infarct zone or whether heightened signal intensities are associated with cytotoxicity such that the heightened intensities are distributed through the left ventricle.

22. The system of claim 17, wherein the at least one processor is configured to determine a potential for a global cardiac injury as the potential of the global injury, and wherein the at least one processor is configured to carry out the autocorrelation by applying an autocorrelation statistic to generate an autocorrelation statistic number (I), with a clustered pattern indicated by an autocorrelation statistic number greater than that associated with a distributed pattern.

23. The system of claim 17, wherein the region of interest is the heart, and wherein the at least one patient image comprises cardiac MRI image slices.

24. The system of claim 17, wherein the at least one processor is configured to detect a global cardiac injury associated with at least one of cardiomyopathy, inflammation, infection, edema or fibrosis.

25. The system of claim 17, wherein the at least one patient image is a plurality of MRI images obtained at intervals prior to and/or after administration of a chemotherapeutic drug, and wherein the at least one processor is configured to apply the autocorrelation to evaluate whether myocellular necrosis is likely to result in a drop in LVEF (left ventricular ejection fraction) as a future onset of the potential global injury.

26. The system of claim 17, wherein the at least onepatient image comprises data from MRI cardiac image slices, and wherein the autocorrelation is carried out to evaluate high intensity voxels/pixels in a left ventricle myocardium, and wherein the at least one processor is configured to identify the potential for global injury when the high intensity voxels/pixels are distributed rather than clustered and predict whether a myocellular injury secondary to a cancer therapy is likely to be associated with a fall in LVEF (left ventricular ejection fraction).

* * * * *

UNITED STATES PATENT AND TRADEMARK OFFICE
CERTIFICATE OF CORRECTION

PATENT NO.        : 8,874,192 B2  
APPLICATION NO.   : 13/961581  
DATED             : October 28, 2014  
INVENTOR(S)       : Hundley et al.

Page 1 of 1

It is certified that error appears in the above-identified patent and that said Letters Patent is hereby corrected as shown below:

In the Claims:
Column 20, Claim 26, Line 8: Delete "at least onepatient"
                              Should read -- at least one patient --

Signed and Sealed this  
Third Day of March, 2015

Michelle K. Lee  
*Deputy Director of the United States Patent and Trademark Office*